United States Patent [19]
Lontine et al.

[11] Patent Number: 6,070,444
[45] Date of Patent: Jun. 6, 2000

[54] METHOD OF MASS MANUFACTURING COATED ELECTROSURGICAL ELECTRODES

[75] Inventors: Michael D. Lontine, Westminster; Gene H. Arts, Berthoud, both of Colo.

[73] Assignee: Sherwood Services AG, Schaffhausen, Switzerland

[21] Appl. No.: 09/282,812

[22] Filed: Mar. 31, 1999

[51] Int. Cl.[7] .................................................. B21B 45/00
[52] U.S. Cl. ................................................................ 72/46
[58] Field of Search .................................. 72/42, 46, 47; 606/41, 42, 43, 44, 45, 46, 47, 48, 49, 50, 51, 52

[56] References Cited

U.S. PATENT DOCUMENTS

| | | |
|---|---|---|
| 3,460,539 | 8/1969 | Anhalt, Sr. . |
| 4,232,676 | 11/1980 | Herczog . |
| 4,314,559 | 2/1982 | Allen . |
| 4,492,231 | 1/1985 | Auth . |
| 4,785,807 | 11/1988 | Blanch . |
| 4,850,353 | 7/1989 | Stasz et al. . |
| 4,862,890 | 9/1989 | Stasz et al. . |
| 5,100,402 | 3/1992 | Fan . |
| 5,197,962 | 3/1993 | Sansom et al. . |
| 5,380,320 | 1/1995 | Morris . |
| 5,382,247 | 1/1995 | Cimino et al. . |
| 5,395,363 | 3/1995 | Billings et al. . |
| 5,403,882 | 4/1995 | Huggins . |
| 5,498,654 | 3/1996 | Shimasaki et al. . |
| 5,549,604 | 8/1996 | Sutcu et al. . |
| 5,643,256 | 7/1997 | Urueta . |
| 5,693,050 | 12/1997 | Speiser . |
| 5,693,052 | 12/1997 | Weaver . |
| 5,697,926 | 12/1997 | Weaver . |
| 5,702,387 | 12/1997 | Arts et al. . |
| 5,713,895 | 2/1998 | Lontine et al. . |
| 5,765,418 | 6/1998 | Rosenberg .................... 72/42 |

*Primary Examiner*—Rodney A Butler

[57] ABSTRACT

A method of mass manufacturing a plurality of electrodes coated with a non-stick layer is disclosed for reducing eschar buildup and the like on the working tip of an electrode during electrosurgical procedures and facilitating ease of cleaning the tip. The plurality of electrodes are mass manufactured for connection to an appropriate electrical power source. One preferred method of mass manufacturing a plurality of electrodes includes the steps of: simultaneously coating at least a portion of a stock material with a non-stick layer; and forming the plurality of electrode blanks having the non-stick layer. The plurality of electrode blanks may be subjected to further finishing. Preferably, the plurality of electrode blanks are formed having the non-stick layer as the material is advanced through a stamping operation. Also, the material may be configured and dimensioned in the form of a tree to provide a plurality of electrode blanks with a non-stick layer.

17 Claims, 6 Drawing Sheets

METHOD OF MASS MANUFACTURING COATED ELECTROSURGICAL ELECTRODES

BACKGROUND

1. Technical Field

The present disclosure relates to coated electrosurgical electrodes and more particularly, to a method of mass manufacturing a plurality of electrosurgical blades having a non-stick coating that resists the build up of eschar and facilitates facile removal of eschar build-up.

2. Background of the Related Art

Electrosurgical electrodes and/or blades are used to cut and coagulate tissue. The electrodes conduct high frequency electrosurgical energy from an appropriate electrical power source to the patient. Many electrically powered instruments using electrosurgical electrodes, such as coagulation forceps, suction cauteries, electrode cautery tips and blades, are well-known.

A working tip of the electrosurgical electrode is subject to high temperatures during use, particularly where an electrosurgical arc is generated, i.e. during fulguration or coagulation. These high temperatures cause the proteins, carbohydrates and lipids in the body to coagulate in the tissue as well as adhere to the working tip. This coagulant is commonly called eschar. Eschar that adheres to the working tip is undesirable because it may reduce cutting and coagulation performance.

Coating an electrosurgical electrode to reduce eschar buildup and make the electrode easier to clean is known in the art. Various coatings are used with medical instruments to render the electrode surface less adherent and facilitate cleaning of the electrode tip. U.S. Pat. No. 4,785,807 discloses an electrosurgical electrode having a first coat of primer material and a second coat of fluorinated hydrocarbon material with RF energy transferred to a treatment site through a capacitive coupling.

Electrosurgical electrodes coated with a non-stick layer may be manufactured individually, i.e., producing one coated electrode per manufacturing process. U.S. Pat. No. 5,702,387 assigned to Valleylab Inc. discloses an electrode blade having a silicone elastomer coating and alternative manufacturing techniques for producing the coated blades, including dip and spray coating the individual blades.

Manufacturing techniques for producing an electrode blade having a nonstick coating, such as those disclosed in U.S. Pat. No. 5,702,387 whereby a single coated electrode is produced per manufacturing process, are expensive and time consuming.

Techniques for producing a plurality of electrodes per manufacturing process are also known. These techniques often utilize automated processes such as feeding a coated coil through a progressive stamping operation. Prior to stamping, the raw material coil is processed in a "coil coating" step whereby the coil is fed through rollers and a non-stick coating is applied to the coil sheet from a coating bath. For example, application Ser. No. 08/367,493 that issued as U.S. Pat. No. 5,713,895 on Feb. 3, 1998, discloses such a manufacturing technique for producing a plurality of electrode blades having a partial non-stick coating whereby conductive sites for contacting tissue may include peaks about the surface of the blade. Adjacent peaks define valleys upon which the non-stick coating primarily resides. That patent is hereby incorporated by reference in its entirety.

The use of a partially coated electrode blade only provides tissue treatment at the exposed conductive sites. In some cases, the limited number of conductive sites may not provide a sufficient tissue treatment area for a particular surgical application, such as, e.g., where a greater amount of tissue requires treatment.

Accordingly, a need exists for a method of mass manufacturing a plurality of electrosurgical electrodes coated with a non-stick layer that provides increased conductive contact area for tissue treatment and advantageously utilizes a mass manufacturing technique that increases the commercial viability of the non-stick coated electrode over the current state of the art.

SUMMARY

A method of mass manufacturing a plurality of electrosurgical electrodes coated with a non-stick layer is disclosed. The non-stick layer reduces eschar buildup and the like on the working tip of an electrode during electrosurgical procedures and facilitates ease of cleaning the tip.

The method of mass manufacturing a plurality of electrosurgical electrodes includes the steps of: providing electrically conductive stock material, coating at least a portion of the stock material with a non-stick layer; and forming a plurality of electrode blanks having the non-stick layer. Thereafter, if desired, the blanks may be subjected to further finishing.

It is contemplated that this method of mass manufacturing a plurality of electrodes may be used to make electrodes for surgical applications whereby each of the plurality of electrodes may be in the form of a blade, a knife, a loop or a ball.

The stock material, preferably, is a medical grade sheet metal adapted for use in surgical applications and configured and dimensioned to provide a plurality of electrode blanks therefrom. Depending on the manner of forming the electrode blanks, various configurations and dimensions may be used for providing the stock material. It is contemplated that the stock material may be provided whereby it is configured and dimensioned in the form of a sheet metal blank, an elongated sheet of sheet metal or as elongated medical grade sheet metal wound into a coil.

The method discloses coating at least a portion of the stock material with a non-stick layer that resists eschar buildup and makes the electrode easier to clean. The step of coating may include spraying, dipping and manually applying a non-stick layer on the material. The non-stick coating may include a synthetic fluorine based resin, polytetrafluoroethylene, fluorinated hydrocarbon, fluoropolymer, silicone, etc. A silicone coating may include, for example, silane, siloxane, polydimethylsiloxane, etc. In an alternate embodiment, the step of coating includes coating substantially all of the stock material with a non-stick layer. Subsequent thereto, a step of finishing is included to selectively remove a portion of the coating thereby exposing stock material for mechanical/electrical connection to a surgical instrument.

Preferably, each of the plurality of electrode blanks formed has a top face and a bottom face coated with a non-stick layer. It is contemplated that, subsequent to forming, each of the plurality of electrodes will have at least one side face exposing raw stock material. Desirably, at least one exposed side face can be adapted for connection to an electrosurgical instrument.

Finishing may include additional coating of one or more side faces with a layer of non-stick material.

The step of finishing also contemplates deburring, buffing, belt grinding, belt sanding or surface grinding the electrode blanks with abrasive material media; plastically deforming, coining, burnishing, embossing, threading, etching, knurling, shot peening, plastically deforming, wire brushing and grit blasting, plasma spraying and electric arc spraying with conductive material; and/or high velocity oxygen fuel spraying at least a portion of each of the plurality of electrode blanks.

BRIEF DESCRIPTION OF THE DRAWINGS

Preferred embodiments of the present disclosure are described herein with reference to the drawings wherein.

DETAILED DESCRIPTION OF PREFERRED EMBODIMENTS

Figure 1:
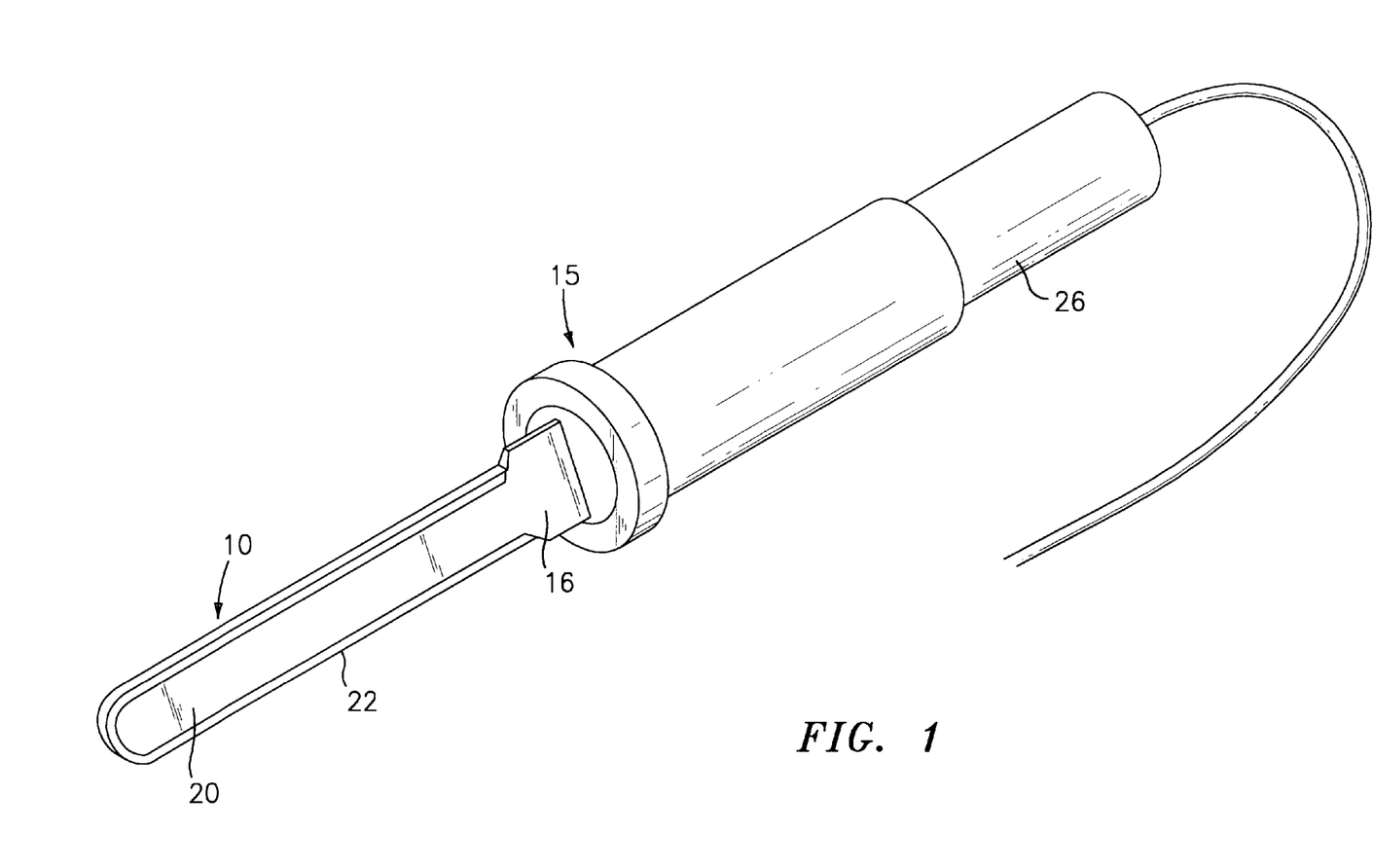
FIG. 1 is a perspective view of a mass manufactured non-stick coated electrosurgical electrode mounted in a handpiece.

Referring to FIG. 1, the present disclosure relates to a method of forming an electrosurgical electrode generally indicated at 10 having a proximal end portion 16 for insertion into a handle 26 or the like and a distal-end portion 20 including a working edge or surface 22 for contacting tissue when the electrosurgical blade 10 is in use.

The proximal end portion 16 is inserted into handle 26 and the appropriate electrical current is supplied from a power source (not shown) in a monopolar or bipolar circuit to the electrosurgical blade 10 or other electrosurgical instrument to cut and/or coagulate a tissue site. Although an electrosurgical blade 10 for cutting and cauterizing is disclosed and described, it is contemplated that the present disclosure is applicable to any electrosurgical instrument that comes into contact with tissue, such as coagulation forceps, suction cautery devices and electrode cautery tips. It is further contemplated that the electrosurgical electrode may comprise various electrosurgical tips such as balls, loops, hooks, etc.

Electrosurgical blade 10 of electrosurgical instrument 15, as illustrated in FIG. 1, connects to a source of electromagnetic energy (not shown) for transmission of electromagnetic energy to the tissue. Non-stick coated electrosurgical electrode 10 applies electromagnetic energy during electrosurgery. Coated electrode 10 and its method of manufacture are described herein.

One preferred method of mass producing a plurality of electrosurgical electrodes includes the steps of: simultaneously coating at least a portion of a conductive stock material with a non-stick layer; and forming the plurality of electrode blanks into electrodes having the non-stick layer. Finishing the plurality of electrode blanks may be accomplished thereafter if necessary, i.e., providing exposed material of the coated stock or deburring.

Figures 2A, 2B, 2C, 2D:
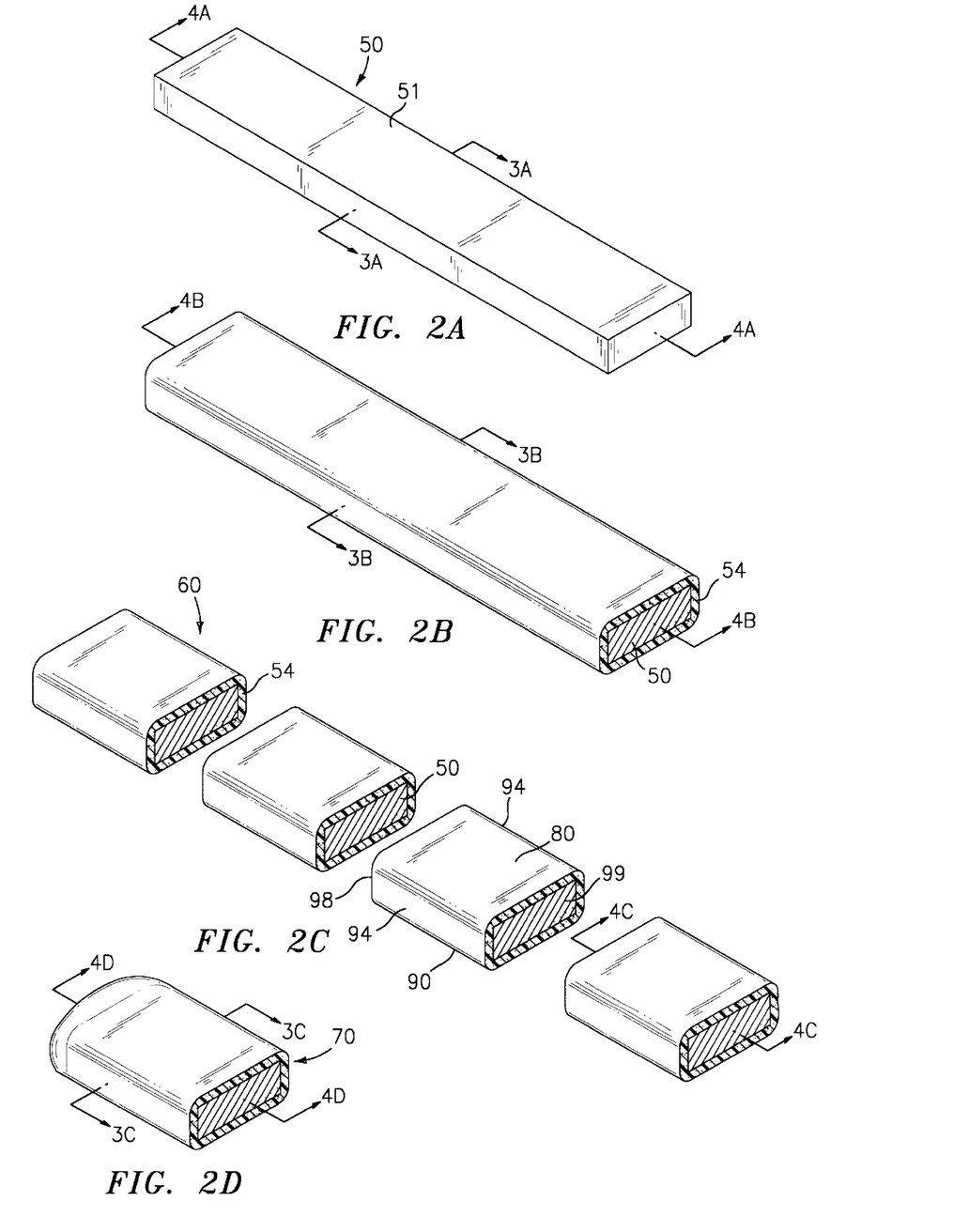
FIGS. 2A–D are illustrations showing an elongate portion of stock material for mass-producing non-stick coated electrosurgical electrodes coated and formed into electrode blanks and finished.

In one embodiment, as shown in FIGS. 2–4, electrosurgical electrode 10 is formed from an elongate stock material 50 (illustrated in FIG. 2A) that is coated with a non-stick layer 54 (illustrated in FIG. 2B) and formed into a plurality of electrode blanks 60 (illustrated in FIG. 2C). Electrode blank 60 may be directly inserted into handle 26 (FIG. 1) for electrical connection thereto or preferably electrode blank 60 may be finished creating electrosurgical electrode 10 (shown in FIG. 1) for insertion into handle 26 or the like.

Figure 3A:
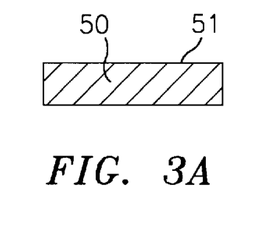
FIGS. 3A–C are cross-sectional views taken along lines 3A—3A, 3B—3B and 3C—3C of FIGS. 2A, 2B and 2D, respectively, showing a product of the method for mass producing the plurality of electrodes with a non-stick coating.
Figure 4A:
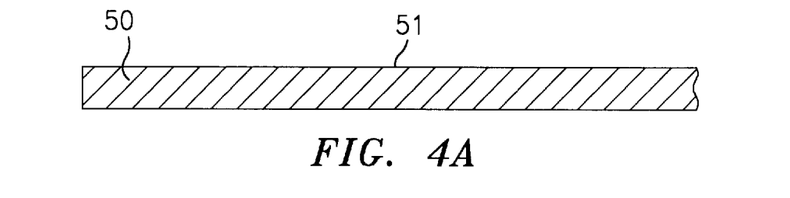
FIGS. 4A–C are a cross-sectional views taken along lines 4A—4A, 4B—4B, and 4C—4C of FIGS. 2A, 2B and 2C, respectively, showing a product of the method for mass producing the plurality of electrodes with a non-stick coating.
Figure 5A:
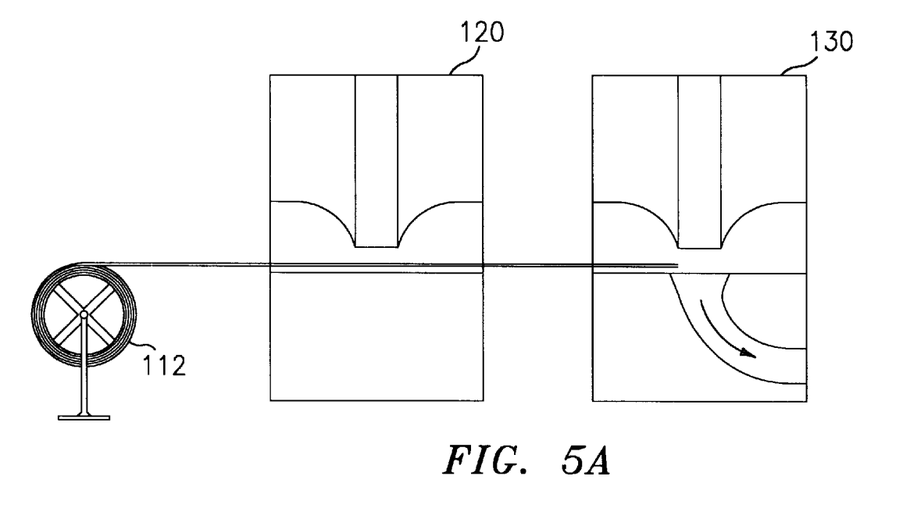
FIG. 5A is a schematic illustration showing a method for mass producing a plurality of non-stick coated electrosurgical electrodes from a sheet metal coil.

Referring to FIGS. 2A, 3A and 4A, stock material 50 is made from medical grade stainless steel or an alloy thereof. Nickel and other highly conductive metals are also acceptable and have been found to work well in electrosurgical applications. Stock material 50 is configured and dimensioned to provide a plurality or electrode blanks 60. In another embodiment, as shown in FIG. 5A, stainless steel stock material 50 is configured and dimensioned as sheet metal in the form of a coil 112. In another embodiment shown in FIG. 5B, stainless steel stock material 50 is configured and dimensioned as sheet metal in the form of an elongated sheet 110. Each embodiment provides stock material 50 for mass manufacture of a plurality of electrode blanks 60.

Figure 3B:
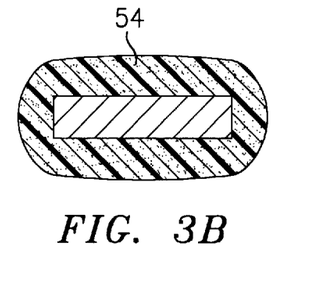
Figure 3C:
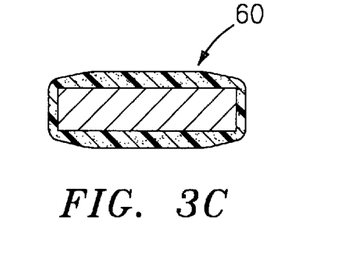
Figure 4B:
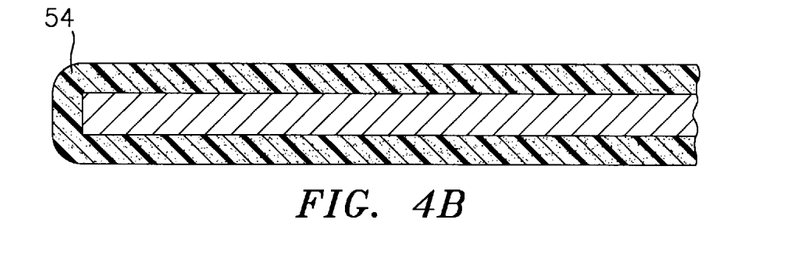

A surface 51, shown in FIGS. 2A, 3A and 4A, of stainless steel stock material 50 is generally smooth with a surface preparation, e.g., chemical etching, abrasive media, etc., so that a substantially uniform layer 54 of non-stick material may be applied. With reference to FIGS. 2B, 3B and 4B, stock material 50 is coated with a non-stick layer 54 for resisting eschar build up and improving ease of cleaning such buildup. The non-stick layer 54 includes a fluoropolymer or silicone layer. It is also contemplated that the non-stick layer may include a synthetic fluorine-based resin, a fluorinated hydrocarbon or silicone elastomers. The coating composition may also contain adhesion promoters, heat stabilizers, fillers, plasticizers, releasor enhancers, cross-linking agents, and colorants. Additionally, these coatings may come in the form of adhesives, dispersions or liquid rubbers.

Figure 4C:
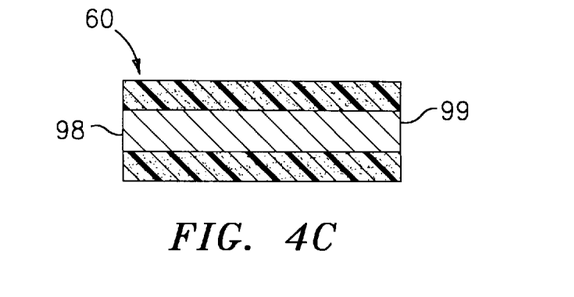

The coating step provides a uniform non-stick layer 54 over stainless steel stock material 50. Material 50 may be coated during a dipping step. The coating step may also include spraying a non-stick layer on the stainless steel material or manually applying a non-stick layer. Preferably, a PTFE non-stick layer has a thickness of at least ½ mil up to a maximum thickness of 3 mils. A non-stick layer including silicone, preferably, has a range of thickness from ½ mil to 10 mils. It is also envisioned that the non-stick layer may be applied to the stock by vapor deposition having a thickness in the micromolecular range to approximately 1/10 mil. It is further contemplated that the layer thickness may be varied at different locations on the stock material depending upon the blade's ultimate use and/or configuration. Subsequent to providing and coating the material, a plurality of electrode blanks 60 are formed from a non-coated stock material, as best shown in FIG. 2C. Formed electrode blanks 60 each have a top face 80, a bottom face 90, side faces 94, 98 and 99. Once formed into individual electrode blanks 60, side faces 98 and 99 will expose raw stock material 50, as shown in FIGS. 2C and 4C. Top face 80, bottom face 90 and side faces 94 remain coated.

Side face 99 exposes raw stock material 50 for contacting tissue to be treated. The remaining side face 98, is inserted into handle 26 for electrical contact and connection with electrosurgical instrument 15. It is envisioned that side faces 94 may also expose raw stock material 50 providing electrical contact and connection with instrument 15 or contact tissue targeted for treatment.

An additional finishing step may include deburring of electrode blank 60 for removing rough portions formed on side faces 98 and 99 during forming.

The step of finishing may also include tumbling the plurality of electrode blanks 60 with abrasive material media such as ceramic, plastic or steel to polish the mass manufactured plurality of electrodes blanks.

The finishing operation may further include buffing, belt grinding, belt sanding, surface grinding, plastic deformation, coining, burnishing, embossing or the like. Manipulating distal end 20 of electrosurgical electrode 10 for its particular application, such as threading, etching, knurling, or stamping is also contemplated.

Figure 5B:
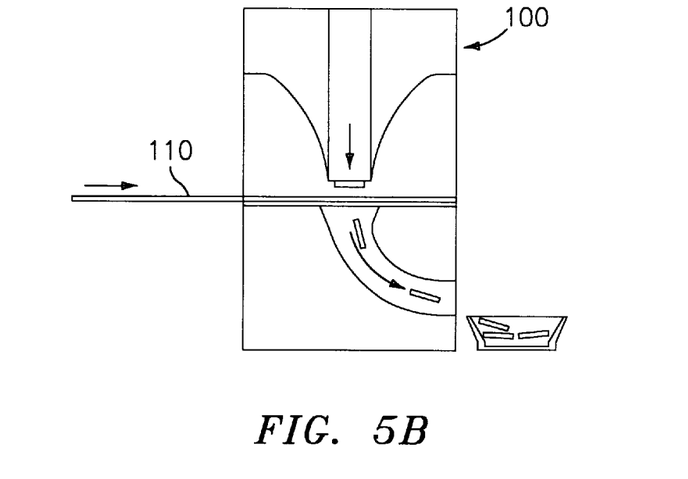
FIG. 5B is a schematic illustration showing a method for mass producing a plurality of non-stick coated electrosurgical electrodes from a sheet metal strip.

In another preferred embodiment, as shown in FIGS. 5A and 5B, the forming step for mass manufacture includes a stamping operation. Stamping press 100 of FIG. 5B forms the plurality of electrode blanks 60 in the stamping operation. Stock material 50 is configured and dimensioned as an elongated sheet 110 to be fed through stamping press 100. Elongated sheet 110 is coated with a non-stick layer 54 prior to forming. Elongated sheet 110 is manually fed into stamping press 100 forming a plurality of electrode blanks 60.

In yet another embodiment shown in FIG. 5A, stock material 50, coated with non-stick layer 54, is configured and dimensioned as a coil 112 that is fed through stamping press 120 and 130 in a progressive stamping operation for forming the plurality of electrode blanks 60. In either of the forming steps, including a stamping operation described above, electrode blanks 60 formed may be finished for use in electrosurgical procedures.

Figures 6A, 6B:
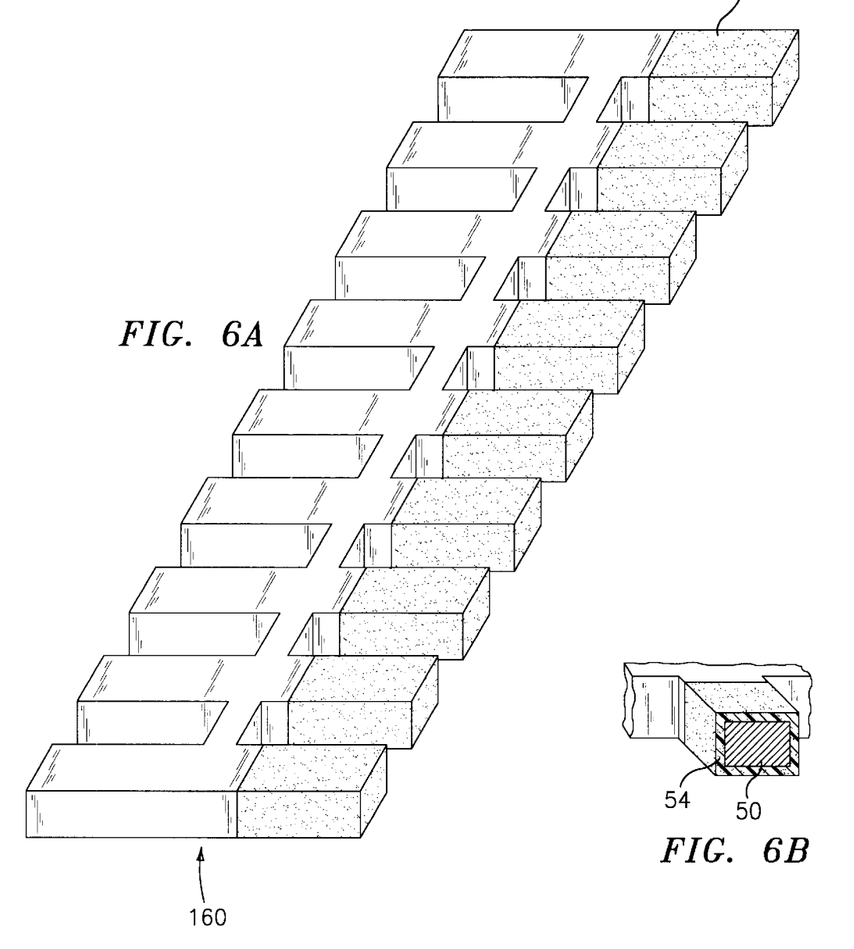
FIG. 6A is a perspective view of stock material configured and dimensioned in the form of a tree to provide a plurality of electrode blanks connected to the tree for mass manufacture.
FIG. 6B is a perspective cut-away view, in part cross-section, of a portion of the tree shown in FIG. 6A subsequent to the step of coating the stock material with a non-stick layer.
Figure 6C:
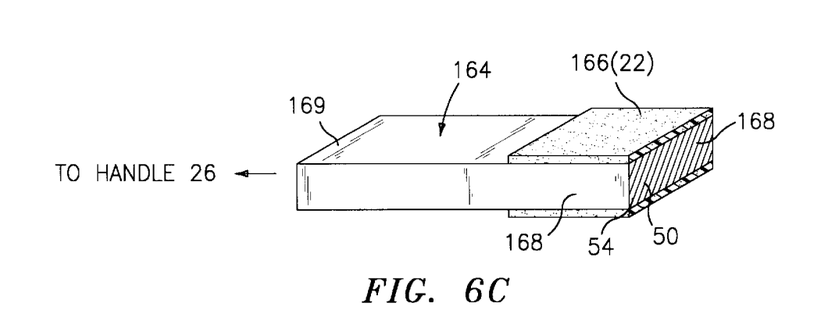
FIG. 6C is a perspective view of one of a plurality of electrodes mass manufactured from stock material configured and dimensioned in the form of a tree.

In another preferred embodiment, stock material 50 is coil formed and configured and dimensioned as a tree 160, as illustrated in FIG. 6A. Tree 160 is partially coated with a non-stick layer 54, as shown in FIG. 6B. Only a portion 161 of tree 160 is coated. It is contemplated that varying portions of tree 160 may be coated for adaptability of tree 160 to various mass manufacturing processes known to one skilled in the art. Electrode blanks 164, illustrated in FIG. 6C, are formed from tree 160. Formed electrode blank 164 has a coated surface 166, further exemplified by non-stick layer 54 and faces 168 exposing raw stock material 50.

It is also envisioned that tree 160 may be provided having substantially all of its outer surface coated with a non-stick layer. Preferably, a subsequent finishing is provided to expose raw stock material.

A proximal end 169 of electrode blank 164 shown in FIG. 6C, corresponding to proximal end portion 16 of electrosurgical electrode 10 of FIG. 1, is directly inserted into handle 26 of electrosurgical instrument 15. Proximal end 169 exposing raw stock material 50 provides an electrical connection for electrosurgical electrode 10 to electrosurgical instrument 15 through handle 26.

An additional step of finishing may be included so that exposed face 169 is prepared for electrical connection to handle 26 of electrosurgical instrument 15 for improved conductivity. The finishing step may include deburring exposed face 168.

Figure 7A:
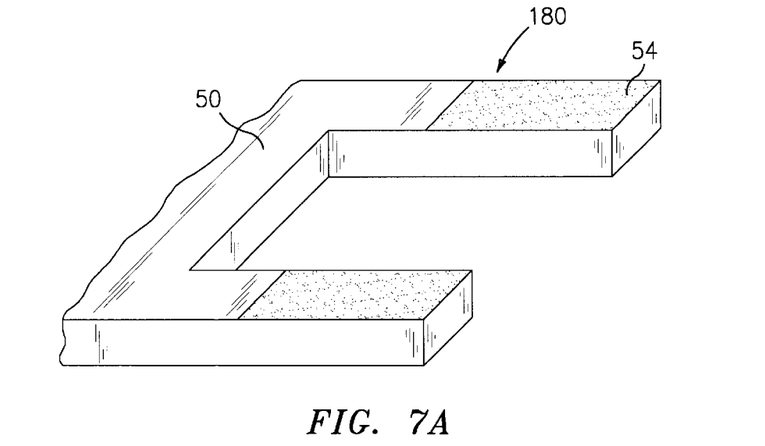
FIG. 7A is a perspective, cut away view of a portion of stock material configured and dimensioned in the form of the tree in FIG. 6A.

In yet another embodiment, a cut away portion 180 of tree 160 (shown in FIG. 6A) is illustrated in FIG. 7A. Stock material 50 having a non-stick layer 54 is configured and dimensioned as tree 160 for mass manufacturing a plurality of electrosurgical electrodes.

Figure 7B:
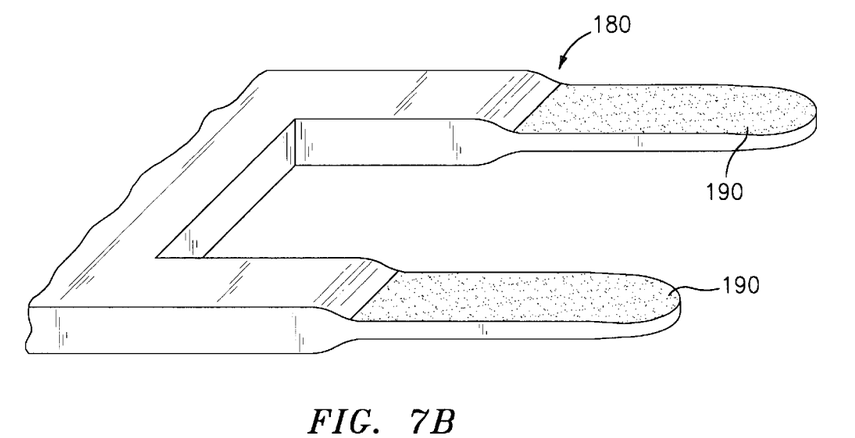
FIG. 7B is a perspective, cut away view of the portion of stock material shown in FIG. 7A after a finishing step is performed.
Figure 7C:
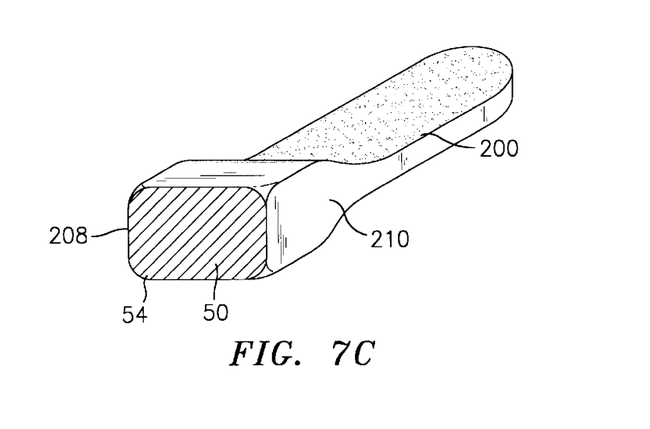
FIG. 7C is a perspective cut away view of a mass manufactured electrode.

As shown in FIG. 7B, tree 160 is finished in a coining operation to embody electrosurgical blanks 190 that are connected to tree 160. Tree 160 may also be finished in a stamping operation or other deforming operation known to one skilled in the art for preparing electrosurgical blanks 190 for the particular electrosurgical application intended. Electrosurgical blades 200 are formed from tree 160, as shown in FIG. 7C. Electrosurgical blade 200 has a face 208 exposing raw stock material 50 for electrical connection to electrosurgical instrument 15 (as shown in FIG. 1). Faces 210 expose raw stock material 50 providing conductive contact sites for treating tissue.

Therefore, it is understood that various modifications may be made to the embodiments disclosed herein. For example, while specific preferred embodiments of the method of mass manufacturing a plurality of electrosurgical electrodes have been described in detail, structures that perform the same function in substantially the same way to achieve substantially the same result may also be used. For example, the stock material may have a rough surface. Further, electrode blanks may contact the tree at more than one face. Therefore, the above description should not be construed as limiting, but merely as exemplifications of preferred embodiments. Those skilled in the art will envision other modifications within the scope and spirit of the present disclosure.

What is claimed is:

1. A method of mass manufacturing a plurality of electrodes, each electrode mass manufactured for connection to an appropriate electrical power source for a surgical procedure, the method comprising the steps of:

provide electrically conductive stock material, whereby the stock material is configured and dimensioned to provide a plurality of electrode blanks;

coating at least a portion of the stock material with a non-stick layer; and forming the plurality of coated electrode blanks wherein each of the plurality of electrode blanks has at least one uncoated side face exposing stock material.

2. The method according to claim 1, further comprising the step of finishing the plurality of electrode blanks.

3. The method according to claim 1, whereby the step of forming includes forming the stock material into a plurality of electrode blades.

4. The method according to claim 1, whereby the step of providing electrically conductive stock material comprises stock material configured and dimensioned as a tree wherein each of the plurality of electrode blanks are connected to the tree by at least one face.

5. The method of manufacturing according to claim 1, wherein the step of providing electrically conductive stock material comprises stock material configured and dimensioned as a sheet that is wound into a coil.

6. The method according to claim 1, wherein the step of providing electrically conductive stock material comprises stock material configured and dimensioned as a sheet in the form of a blank.

7. The method according to claim 1, wherein the step of coating comprises the step of coating the stock material with at least one non-stick layer selected from the group consisting of synthetic fluorine based resins, fluorinated carbons and silicone elastomers.

8. The method according to claim 1, wherein the step of forming comprises a stamping operation.

9. The method according to claim 2, wherein the step of finishing includes coating any of the uncoated side faces exposing stock material with a layer of non-stick material.

10. The method according to claim 7, wherein the non-stick layer comprises polytetrafluoroethylene.

11. A method of mass manufacturing a plurality of electrodes, each electrode mass manufactured for connection to an appropriate electric power source for a surgical procedure, the method comprising the steps of:

providing electrically conductive stock material, whereby the stock material is configured and dimensioned to provide a plurality of electrode blanks;

coating at least a portion of the stock material with a non-stick layer;

feeding the stock material having the non-stick layer to a stamping operation, wherein the stock material is configured and dimensioned for receipt by the stamping operation;

forming the plurality of electrode blanks having the non-stick layer;

wherein the plurality of electrode blanks are formed having the non-stick layer as the material is advanced through the stamping operation, wherein each of the plurality of electrode blanks has at least one uncoated side face exposing stock material; and finishing the plurality of electrode blanks.

12. The method according to claim 11, wherein the step of providing electrically conductive stock material further comprises stock material configured and dimensioned as a coil of sheet metal, the step of feeding further comprises configuring the coil for the stamping operation, and the step of forming further comprises advancing the coil through the stamping operation.

13. The method according to claim 11, wherein the step of providing electrically conductive stock material further comprises stock material configured and dimensioned as an elongated sheet metal, the step of feeding further comprises adapting the elongated sheet for the stamping operation, and the step of forming further comprises advancing the elongated sheet through the stamping operation.

14. The method according to claim 11, wherein the step of providing electrically conductive stock material further comprises the material configured and dimensioned as a sheet metal blank and the step of feeding further comprises adapting the sheet metal blank for use with the stamping operation.

15. A method of mass manufacturing a plurality of electrodes, each electrode mass manufactured for connection to an appropriate electrical power source for a surgical procedure, the method comprising the steps of:

providing electrically conductive stock material, whereby the stock material is configured and dimensioned as a tree to provide a plurality of electrode blanks, whereby each of the plurality of electrode blanks are connected to the tree by at least one face;

coating at least a portion of the tree with a non-stick layer; and forming the plurality of electrode blanks having the non-stick layer.

16. The method according to claim 15, further comprising the step of finishing the tree.

17. The method according to claim 16, wherein the step of finishing the tree comprises removing at least a portion of the coating.

* * * * *